United States Patent [19]

Müller et al.

[11] Patent Number: 5,068,264
[45] Date of Patent: Nov. 26, 1991

[54] FORMYLPIPERAZINYL-(METH)ACRYLIC ACID DERIVATIVES FOR TREATMENT OF COLLAGEN

[75] Inventors: Michael Müller, Bergisch-Gladbach; Wolfgang Podszun, Cologne, both of Fed. Rep. of Germany

[73] Assignee: Bayer Aktiengesellschaft, Leverkusen, Fed. Rep. of Germany

[21] Appl. No.: 509,000

[22] Filed: Apr. 12, 1990

[30] Foreign Application Priority Data

Apr. 27, 1989 [DE] Fed. Rep. of Germany ....... 3913940

[51] Int. Cl.$^5$ .................. A61K 6/00; A61L 15/58; C07D 241/04
[52] U.S. Cl. .................... 522/167; 433/226; 433/228.1; 523/116; 523/118; 544/386; 544/391
[58] Field of Search ................ 523/118, 116; 522/167

[56] References Cited

U.S. PATENT DOCUMENTS

| | | | |
|---|---|---|---|
| 4,380,432 | 4/1983 | Orlowski et al. ................ | 523/118 |
| 4,456,603 | 6/1984 | Yamatsu et al. ................ | 544/386 |
| 4,804,412 | 2/1989 | Komiyama et al. ............. | 523/118 |

FOREIGN PATENT DOCUMENTS

| | | |
|---|---|---|
| 0141324 | 5/1985 | European Pat. Off. . |
| 2507189 | 9/1976 | Fed. Rep. of Germany . |
| 2550547 | 5/1977 | Fed. Rep. of Germany . |
| 3703080 | 1/1988 | Fed. Rep. of Germany . |
| 742450 | 12/1955 | United Kingdom . |

OTHER PUBLICATIONS

Naarmann et al., "Chemical Abstracts", vol. 77, 1972, Col. 89097x.

*Primary Examiner*—C. Warren Ivy
*Assistant Examiner*—James H. Turnipseed
*Attorney, Agent, or Firm*—Sprung Horn Kramer & Woods

[57] ABSTRACT

The invention relates to new formylpiperazine group-containing (meth)acrylic acid esters and (meth)acrylamides (I) of the general formula (L)

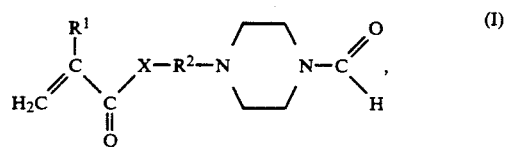

in which
 $R^1$ is hydrogen or methyl,
 $R^2$ is a divalent aliphatic or cycloaliphatic radical, and
 X is —O— or —NH—, and to preparations which contain these compounds, for use as adhesive component for the treatment of collagen-containing materials, and to processes for the preparation and to the use of the preparations.

9 Claims, No Drawings

FORMYLPIPERAZINYL-(METH)ACRYLIC ACID DERIVATIVES FOR TREATMENT OF COLLAGEN

The invention relates to new formylpiperazine group-containing (meth)acrylic acid derivatives of the formula (I) and preparations, which contain these compounds, for use as adhesive components for the treatment of collagen-containing materials, and to processes for the preparation and to the use of the preparations.

The new formylpiperazine group-containing (meth)acrylic acid esters and (meth)acrylamides correspond to the formula (I)

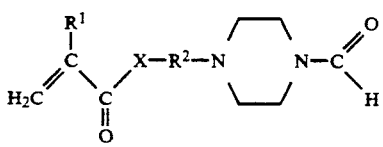

in which $R^1$ denotes hydrogen or methyl, $R^2$ denotes a divalent aliphatic or cycloaliphatic radical and X has the meaning of —O— or —NH—.

The invention additionally relates to preparations, which contain compounds (I), and, if appropriate, initiators and solvent for use as adhesive component for the treatment of collagen-containing materials, to processes for the preparation and to the use of the preparations.

Collagen-containing materials are albuminoid bodies and principal constituents of the human and animal intercellular supporting substances, such as cartilage and bone tissue, skin and dentine. In the context of the present invention, the adhesive components are preferably used for the treatment of dentine in connection with dental repairs.

Particularly in the dental field, setting polymeric materials are used as filling materials in dental repairs. In general, fillings based on acrylates are preferred as setting polymeric materials. However, these polymeric fillings have the disadvantage that they adhere poorly to the dentine. In order to solve this problem, investigations on the dental bone have previously sometimes been carried out; for this purpose it was necessary to remove considerable amounts of fresh dentine beyond the affected region.

According to another method, the dentine and the enamel surface are etched with acids, such as, for example, phosphoric acid, and the filling is then performed. Apart from the fact that the acid exerts an irritant action in the oral region, it also penetrates easily into the tooth through the dental tubules and damages the nerve (pulp).

In J. Dent. Res. 57, 500–505 (1978), aldehyde group-containing methacrylates of the isomeric hydroxybenzaldehydes are described which can be used as foundations for fillings in the dental field. However, even after such a foundation, the bond between dentine and filling material remains unsatisfactory.

In Scand. J. Dent. Res. 92, 480–483 (1984) and J. Dent. Res. 63, 1087–1089 (1984), foundations based on aqueous formaldehyde or glutaraldehyde and β-hydroxyethyl methacrylate (HEMA) are described.

In addition, compositions formed from an aldehyde and an olefinically unsaturated monomer containing active hydrogen, which bond well to dentine, are described in U.S. Pat. No. 4,593,054.

The new preparations based on formylpiperazine group-containing (meth)acrylic acid esters or (meth)acrylamides effect a strong adhesive bonding of materials which are intended to be attached to collagen, for example an adhesive bonding of dental filling material in a cavity in the tooth.

Formamide group-containing (meth)acrylic acid alkyl esters are known from U.S. Pat. No. 4,039,513. In DE-A-2,507,189 the use of these acrylic acid esters as coatings or adhesives for paper and textiles is also described.

The use of the N-formyl-N'-[(meth)acryloyloxyalkyl]piperazines and N-formyl-N'-[(meth)acryloylaminoalkyl]piperazines (I) according to the invention as adhesive component for collagen-containing materials was surprising since they contain no reactive groups which under mild conditions can build up suitable chemical bonds to give collagen-containing materials.

(Meth)acrylic acid esters and (meth)acrylamides in the context of the present invention are the esters and amides of acrylic acid and of methacrylic acid.

A divalent aliphatic radical ($R^2$) in general denotes a divalent, straight-chain or branched hydrocarbon radical having 1 to 6, preferably 1 or 2, carbon atoms.

Examples which may be mentioned are the following divalent aliphatic radicals: hexanediyl, pentanediyl, neopentanediyl, butanediyl, dimethylethanediyl, propanediyl and ethanediyl.

A divalent cycloaliphatic radical ($R^2$) in general denotes a cyclic hydrocarbon radical having 4 to 6 carbon atoms. Examples which may be mentioned are the following divalent cycloaliphatic radicals: cyclobutanediyl, cyclopentanediyl and cyclohexanediyl.

The following formylpiperazine group-containing (meth)acrylic acid esters and (meth)acrylamides may be mentioned as examples:

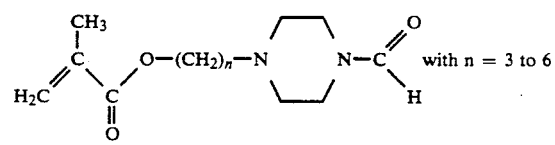

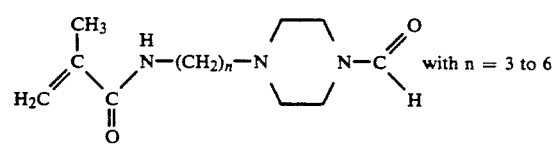

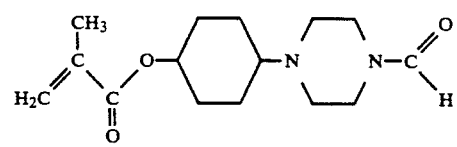

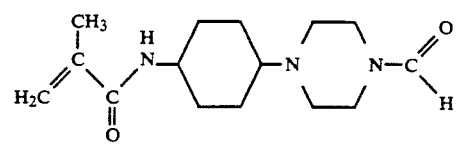

N-Formyl-N'-(methacryloyloxyethyl)piperazine and N-formyl-N'-(methacryloylaminoethyl)piperazine of the formulae

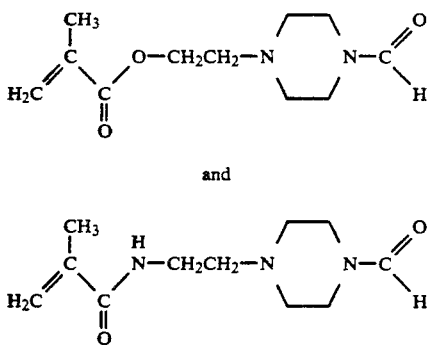

and are particularly preferred.

For example, the N-formyl-N'-[(meth)acryloyloxyalkyl]piperazines according to the invention can be prepared by reaction of N-(hydroxyalkyl)piperazines with formic acid esters and (meth)acryloyl chloride.

N-formyl-N'-[(meth)acryloylaminoalkyl]piperazines can surprisingly be prepared by corresponding successive reaction of N-(aminoalkyl)piperazines (II) with formic acid alkyl esters (III) and (meth)acryloyl chloride (IV):

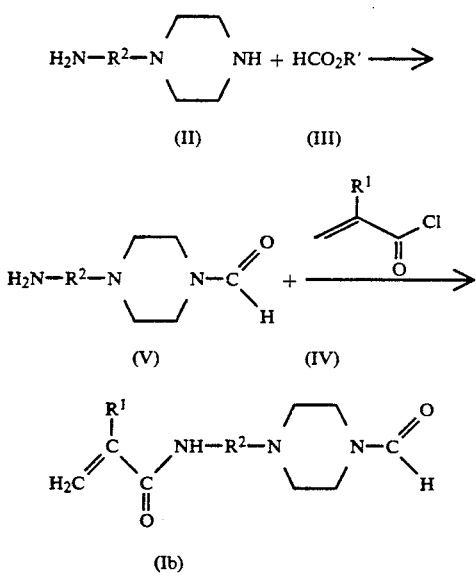

The invention additionally relates to the new N-formyl-N'-aminoalkylpiperazines (V) obtained as intermediates. These compounds were unable to be obtained previously since the aminoalkylpiperazines (II) were not able to react selectively on the secondary N atom with formic acid phenyl esters ( DE-OS(German Offenlegungsschrift 2209853)(GB 1388917) ) or also with free carboxylic acids (U.S. Pat. No. 3,385,858).

It has now been found that this formylation of aminoalkylpiperazines (II) with formic acid alkyl esters III) can be carried out in high selectivity to give the N-formyl-N'-aminoalkylpiperazines (V) according to the invention.

For this purpose, formic acid esters of short chain alcohols such as butyl formates or propyl formates are advantageously employed. Methyl formates or ethyl formates are particularly preferred.

The intermediates (V) according to the invention not only important for the preparation of N-formyl-N'-[(methyl)acryloylaminoalkyl]-piperazines (Ib), but can also be employed as intermediates for active compound syntheses.

Initiators in the context of the present invention are free radical formers which induce a free radical polymerization. Photoinitiators, which induce a free radical polymerization under the action of light, for example UV light, visible light or laser light, are preferred.

The so-called photopolymerization initiators are known per se (Houben-Weyl, Methoden der organischen Chemie (Methods of Organic Chemistry), Volume E 20, page 50 et seq, Georg Thieme Verlag Stuttgart 1987). Preferably, these are mono- or dicarbonyl compounds, such as benzoin and its derivatives, in particular benzoin methyl ether, benzil and benzil derivatives, for example 4,4-oxydibenzil and other dicarbonyl compounds such as diacetyl, 2,3-pentanedione and α-diketo derivatives of norbornane and substituted norbornanes, metal carbonyls such as manganese pentacarbonyl or quinones such as 9,10-phenanthrenequinone and naphthquinone. Camphorquinone is particularly preferred.

The preparations according to the invention in general contain 0.01 to 2 parts by weight, preferably 0.2 to 0.5 parts by weight of the initiator, relative to 1 part by weight of the N-formylpiperazine group-containing (meth)acrylic acid esters or (meth)acrylamides.

If one of the parts to be joined which is in contact with the adhesive component according to the invention already contains an initiator of the type described, the initiator in the adhesive component can even be completely dispensed with.

The solvents in the context of the present invention should dissolve the component and, because of the application, should be non-toxic. Water and volatile organic solvents such as methanol, ethanol, propanol, isopropanol, acetone, methyl ethyl ketone, tetrahydrofuran, methyl acetate or ethyl acetate may be mentioned as preferred.

In general, 10 to 1000 parts by weight, preferably 50 to 300 parts by weight, of the solvent are employed, relative to the N-formylpiperazine derivatives.

It may be advantageous to add coactivators, which accelerate the polymerization reaction, to the preparations according to the invention. Known accelerators are, for example, amines such as p-toluidine, dimethyl-p-toluidine, trialkylamines such as trihexylamine, polyamines such as N,N,N',N'-tetraalkylalkylenediamine, barbituric acid and dialkylbarbituric acid.

The coactivators are in general employed in an amount from 0.02 to 4 % by weight, preferably 0.2 to 1 % by weight, relative to the amount of polymerizable compounds.

The compositions according to the invention may contain carbonyl compounds as a further component.

Carbonyl compounds in the context of the present invention are aldehydes and ketones which contain 1 to 20, preferably 1 to 10, and particularly preferably 2 to 6 carbon atoms. The carbonyl function can be bonded to an aliphatic, aromatic and heterocyclic molecule moiety.

Aldehydes which may be mentioned are aliphatic mono- or dialdehydes. Formaldehyde, acetaldehyde, propionaldehyde, 2-methylpropionaldehyde, butyraldehyde, benzaldehyde, vanillin, furfural, anisaldehyde, salicylaldehyde, glyoxal, glutaraldehyde and phthalaldehyde are preferred. Glutaraldehyde is particularly preferred.

Ketones which may be particularly mentioned are aliphatic mono- and diketones. Butanone, acetone, cyclooctanone, cycloheptanone, cyclohexanone, cyclopentanone, acetophenone, benzophenone, 1-phenyl-2-propanone, 1,3-diphenyl-2-propanone, acetylacetone, 1,2-cyclohexanedione, 1,2-cyclopentanedione and camphorquinone are preferred. Cyclopentanone is particularly preferred.

In general, 1 to 1000 parts by weight, preferably 5 to 50 parts by weight, of the carbonyl compounds are employed, relative to the N-formylpiperazine derivatives.

A further component, the compositions according to the inventions can contain (meth)acrylic acid esters which can form cross-linkages. (Meth)acrylic acid esters which can form cross-linkages in general contain 2 or more polymerizable active groups in the molecule. Esters of (meth)acrylic acid with dihydric to pentahydric alcohols containing 2 to 30 carbon atoms may be mentioned as preferred. Alkoxy(meth)acrylates and urethane group-containing (meth)acrylates are particularly preferred.

(Meth)acrylic acid esters of the formula

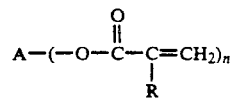

in which

A denotes a straight-chain, branched, cyclic, aliphatic, aromatic or mixed aliphatic-aromatic radical having 2 to 25 C atoms, which can be interrupted by —O—, NH— or O—CO—NH— bridges and can be substituted by hydroxyl, oxy, carboxyl, amino or halogen, R denotes H or methyl and n represents an integer from 2 to 8, preferably 2 to 4, may be mentioned as examples.

Compounds of the following formulae:

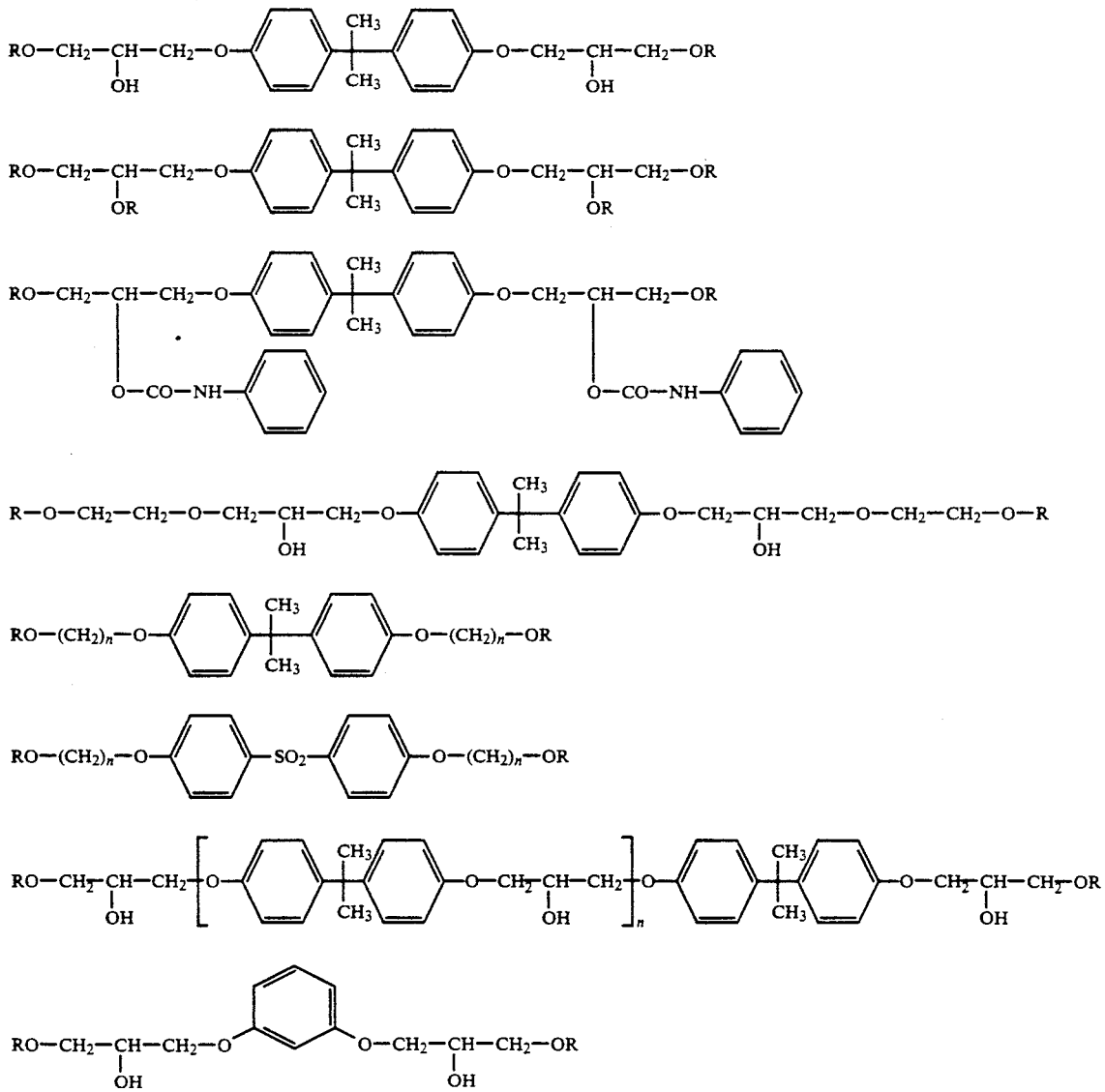

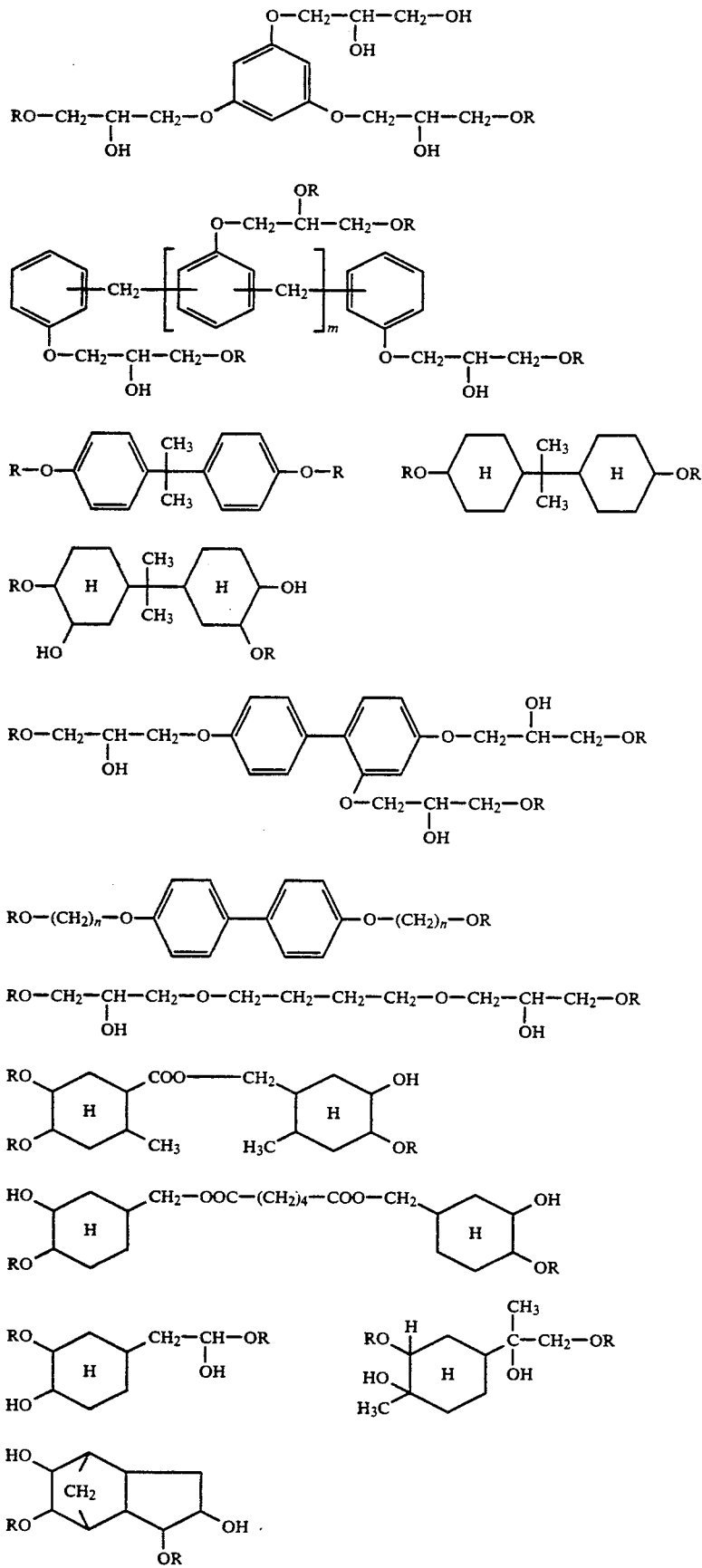

-continued

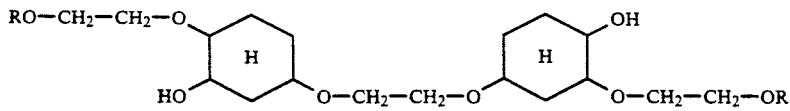

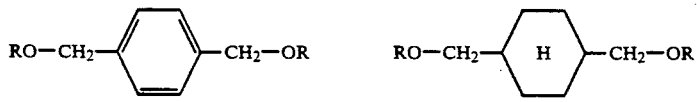

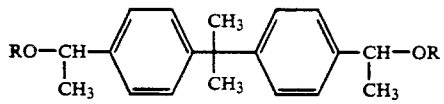

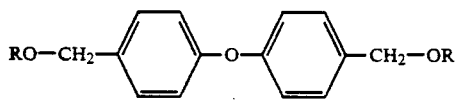

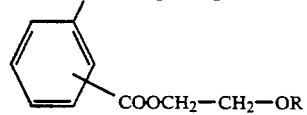
in the ortho-, meta-, or para-form

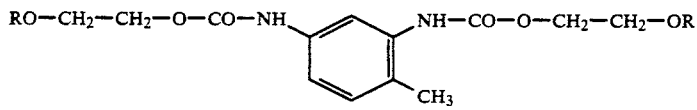

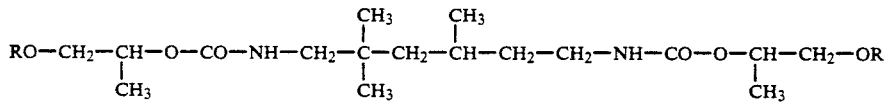

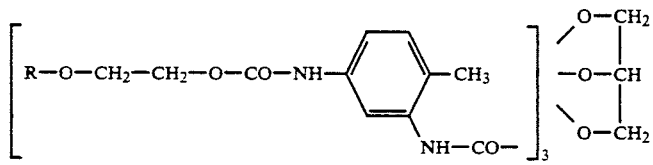

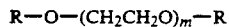

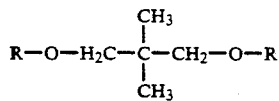

in which
R represents

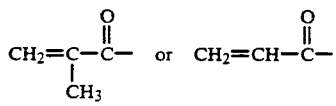

n denotes a number from 1 to 4 and
m denotes a number from 0 to 5,
may be mentioned as preferred.

In addition, derivatives of tricyclodecane (U.S. Pat. No. 4,323,696) and reaction products of polyols, diisocyanates and hydroxyalkyl methacrylates (EP 254185, EP 254950 and U.S. Pat. No. 4,879,402) may be mentioned. The following monomers may be mentioned as examples:

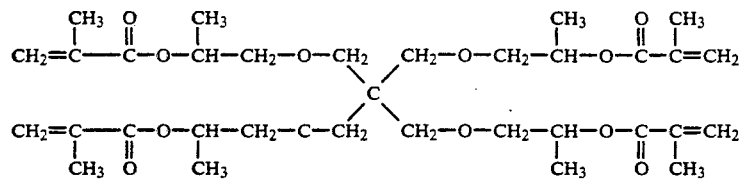
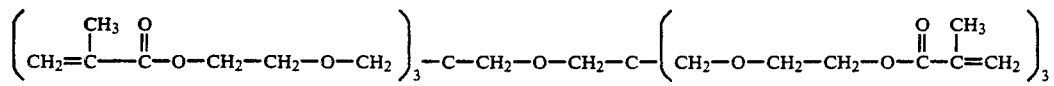
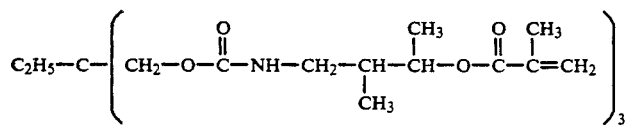
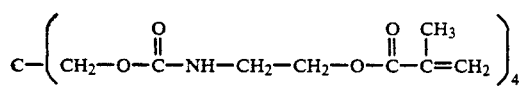
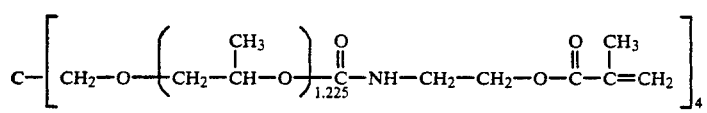
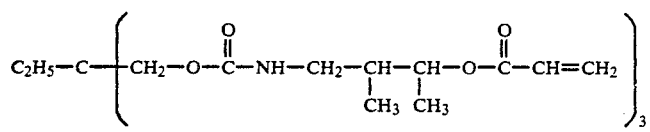
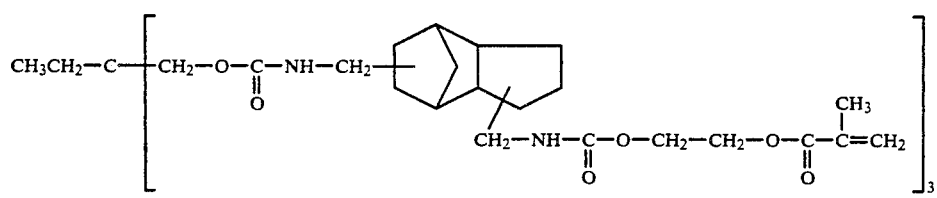
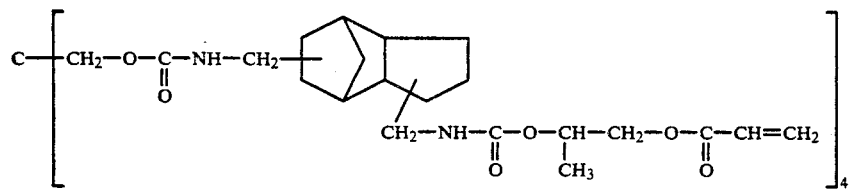
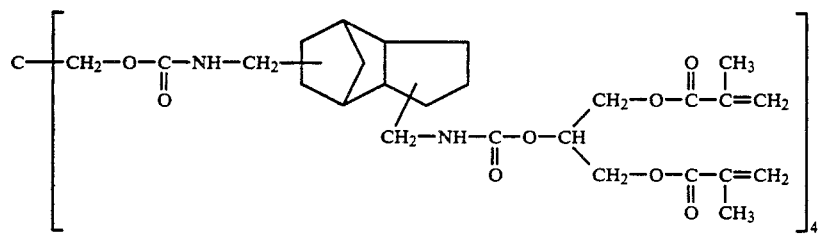

-continued
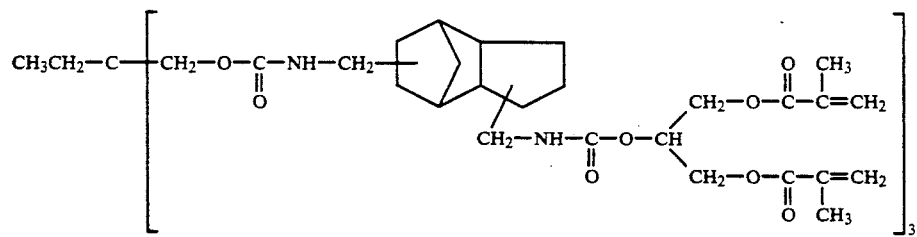
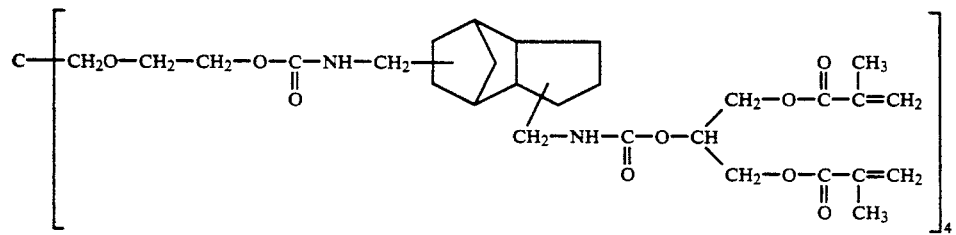
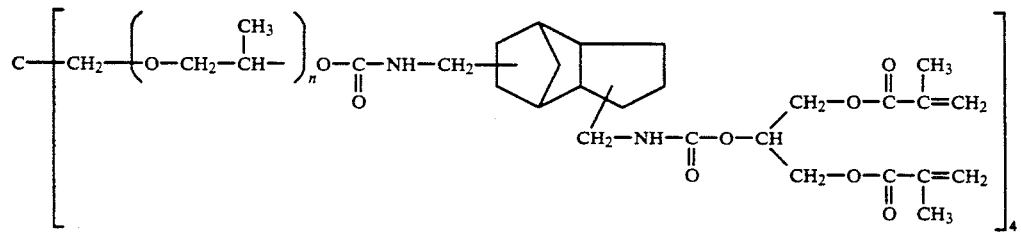
n = 1.225 (statistical mean for 4 chains)
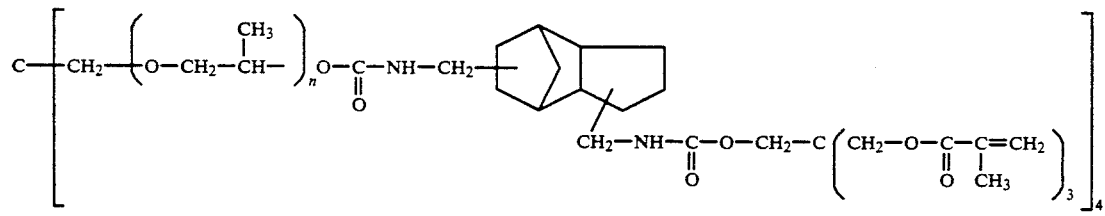
n = 1.225 (mean)
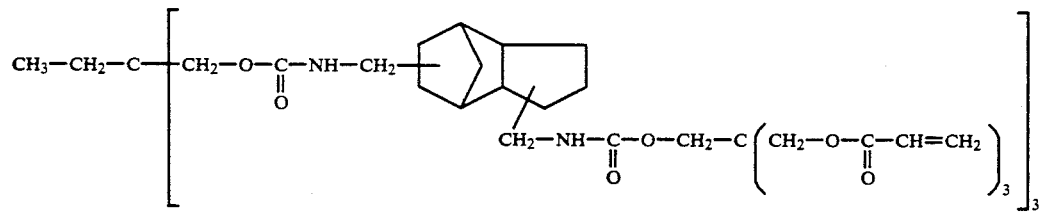
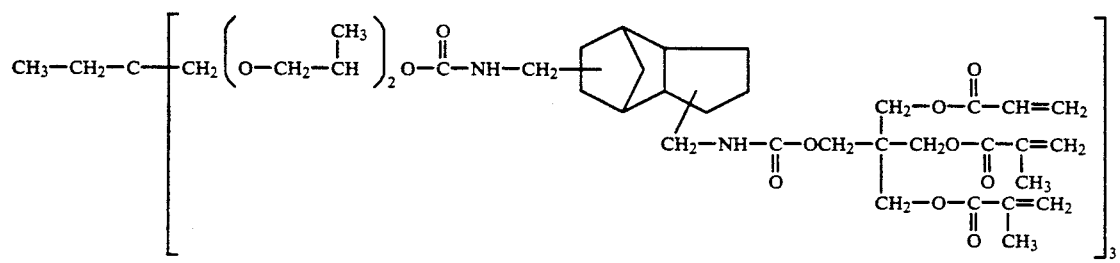

-continued
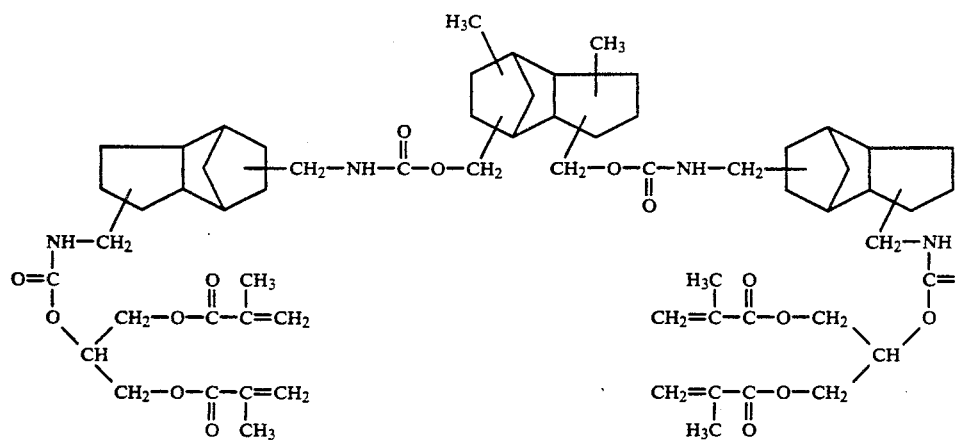
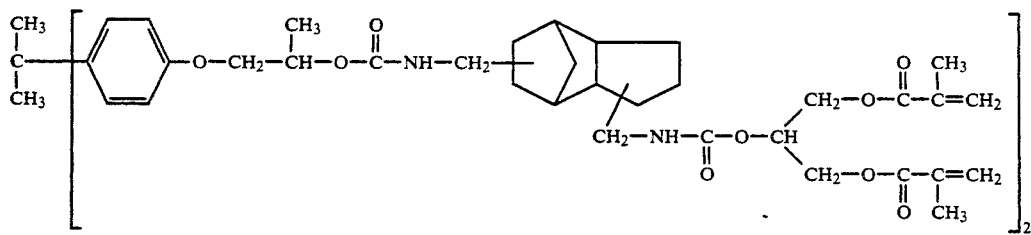
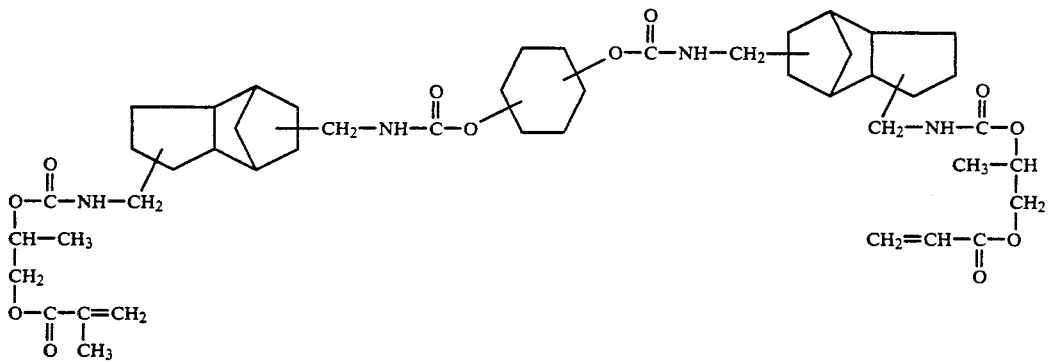
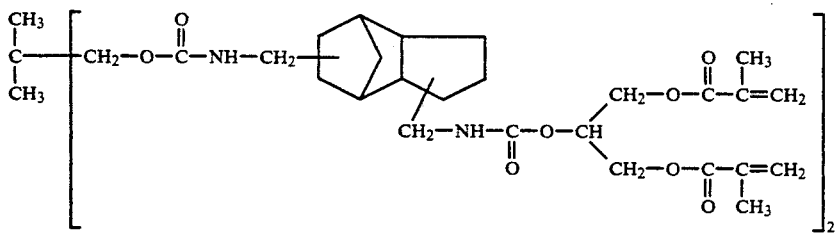
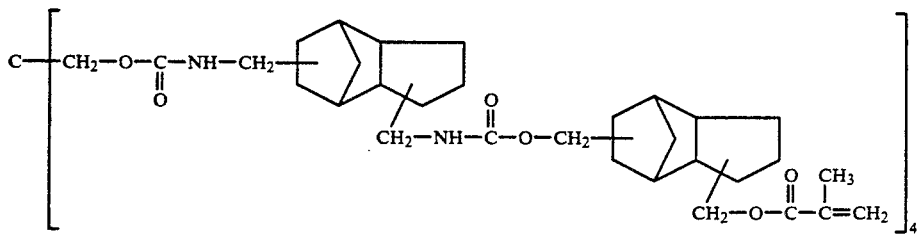

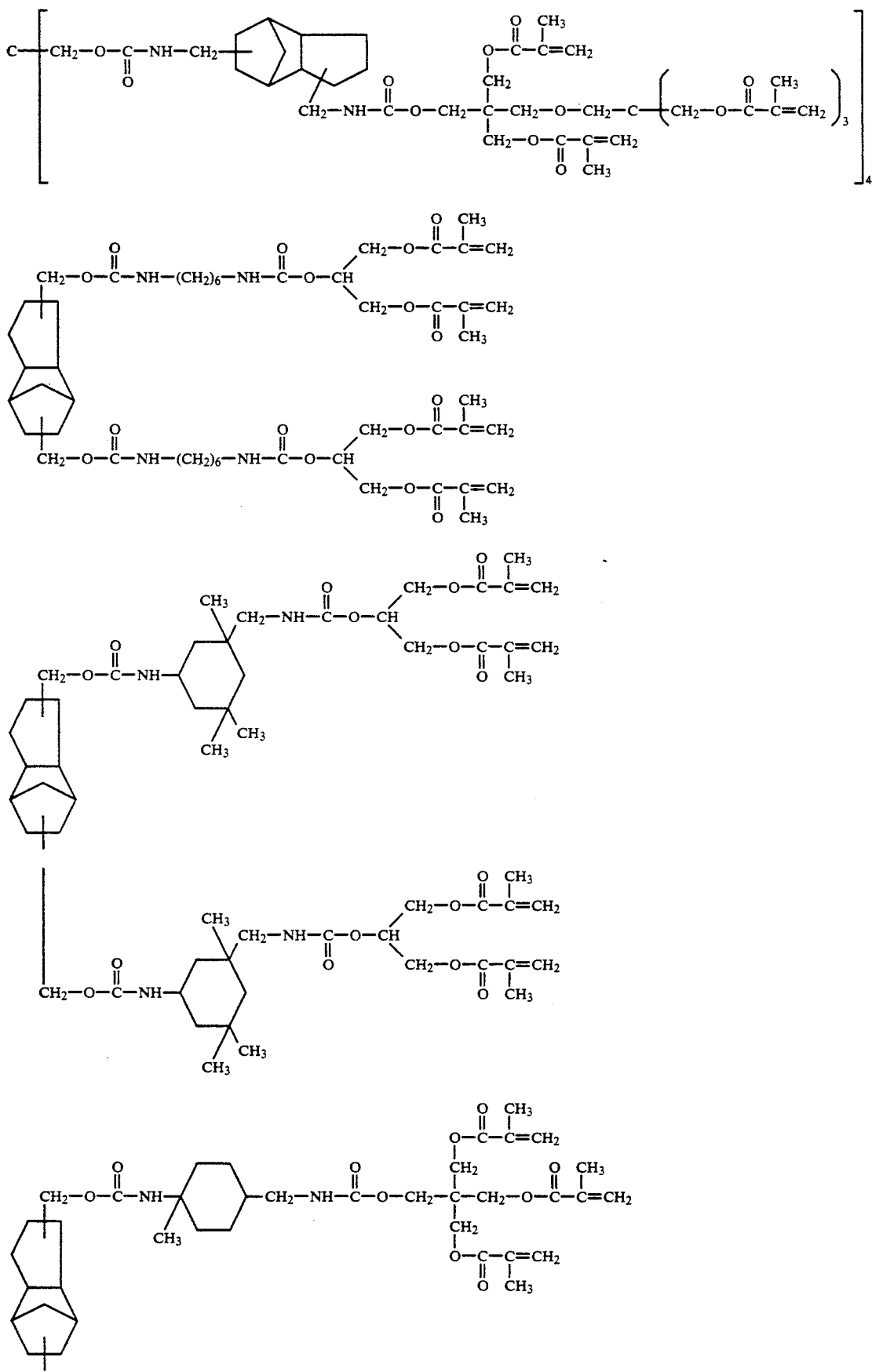

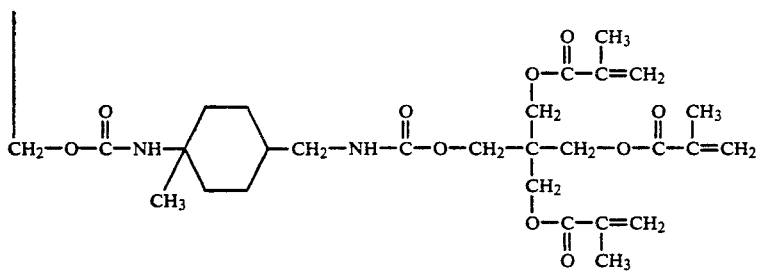

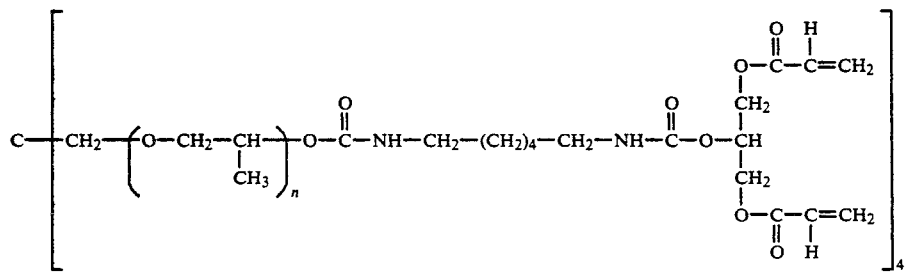

n = 1.225 (statistical mean for 4 chains)

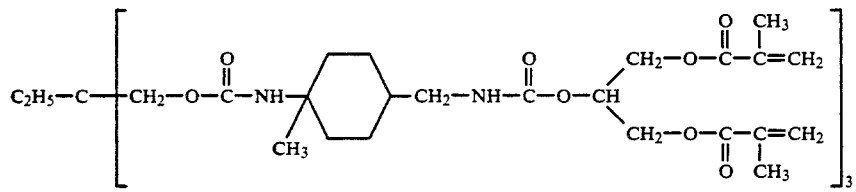

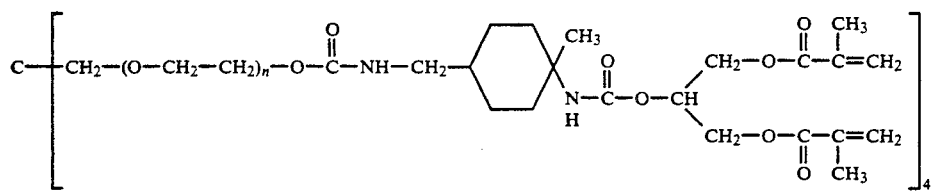

n = 1.225 (statistical mean for 4 chains)

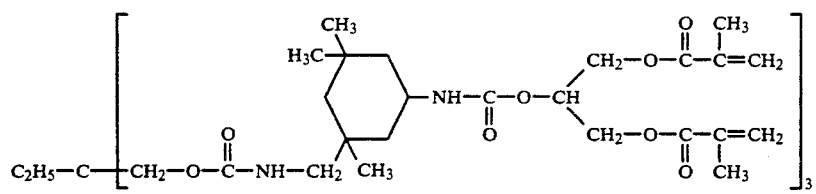

The so-called bis-GMA of the formula

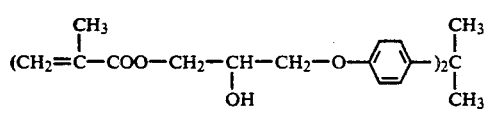

is particularly preferred as a monomer.

Of course, it is possible to employ mixtures of the various (meth)acrylic acid esters which can form cross-linkages. Mixtures of 20 to 70 parts by weight of bis-GMA and 30 to 80 parts by weight of triethylene glycol dimethacrylate may be mentioned as examples.

The preparations according to the invention in general contain 5 to 80 parts by weight, preferably 10 to 60 parts by weight, of carboxyl compounds, relative to the N-formylpiperazine derivatives.

The compositions according to the invention may contain fillers as further component. Fine powders which have a particle diameter in the range from 0.1 to 100 μm (if appropriate also in a polydisperse distribution) are preferred as fillers. Fillers may be fillers customary in the dental field (R. S. Baratz, J. Biomat. Applications, Vol 1, 1987, p 316 et seq.) such as inorganic glasses, silica, alumina or quartz powder.

As a result of a proportion of fillers in the preparations according to the invention, adhesive cements result which are particularly suitable for attaching bridges, crowns and other facing materials.

The proportion of the filler is in general 20 to 80 parts by weight, preferably 40 to 70 parts by weight, relative to the total preparation.

The adhesive components according to this invention may furthermore contain up to 10 parts by weight of customary additives such as stabilisers, inhibitors, light screens, colorants, pigments or fluorescent substances.

The preparations according to the invention can be prepared by mixing the formylpiperazine group-containing (meth)acrylic acid esters or (meth)acrylamides and the initiator and, if appropriate, the other components by vigorous stirring.

The preparations may also be solvent-free.

The preparations according to the invention can be used as adhesive component for the treatment of collagen-containing materials.

In a particular embodiment, the collagen-containing material is conditioned before the treatment with the preparation according to the invention using a liquid having a pH value in the range from 0.1 to 3.5.

This liquid in general contains acids having a pK value of less than 5 and, if appropriate, an amphoteric amino compound having a $pK_a$ value in the range from 9.0 to 10.6 and a $pK_B$ value in the range from 11.5 to 12.5. The conditioning liquid may contain, for example, the following acids: phosphoric acid, nitric acid, pyruvic acid, citric acid, oxalic acid, ethylenediaminetetraacetic acid, acetic acid, tartaric acid, malic acid and maleic acid.

Amphoteric amino compounds which may be mentioned are preferably compounds of the formula $$R^2-\overset{\overset{H}{|}}{\underset{\underset{R^3-NH}{|}}{C}}-R^1$$

in which $R^1$ represents a carboxyl group, $R^2$ denotes hydrogen, or a lower alkyl radical optionally substituted by hydroxyl, thio, methylthio, carboxyl, amino, phenyl, hydroxy-phenyl or the groups $R^3$ denotes hydrogen or phenyl, where the radicals $R^1$ and $R^3$ can form a propylene radical, or in which $R^1$ represents hydrogen, $R^2$ represents the group $$-A-NH_3X$$

in which

A represents a doubly bonded alkylene radical having 1 to 6 carbon atoms and

X represents halogen, and $R^3$ denotes hydrogen.

The following amphoteric amino compounds may be mentioned as examples: glycine, serine, threonine, cysteine, tyrosine, asparagine, glutamine, alanine, valine, leucine, isoleucine, proline, methionine, phenylalanine, tryptophan, lysine, arginine, histidine, N-phenylglycine, ethylenediamine hydrochloride, ethylenediamine hydrobromide, propylenediamine hydrochloride, propylenediamine hydrobromide, butylenediamine hydrochloride, butylenediamine hydrobromide, leucine hydrochloride and histidine hydrochloride.

The conditioning liquid may furthermore contain substances from the group comprising the polyethylene glycols and metal hydroxides. In particular the above-mentioned polybasic acids can also be employed partly as metal salts as long as free acid functions remain.

Conditioning liquids which contain at least one of the acids from the group comprising pyruvic acid, ethylenediaminetetraacetic acid and citric acid and, if appropriate, an amphoteric amino compound from the group comprising glycine, N-phenylglycine and proline, are particularly preferred.

The application of the preparations according to the invention can be carried out, for example, as follows: In a dental repair, for example, after a mechanical cleaning of the collagen-containing dental material, the conditioning fluid is first applied using some absorbent cotton and allowed to act for a short time (for example 60 seconds), and the dental material is rinsed with water and dried in a stream of air. The preparation according to the invention is then applied in a thin layer, for example using a small brush, and dried in a stream of air. After the treatment according to the invention, the actual filling material, for example plastic filling materials customary in the dental field (K. Eichner, "Zahnärztliche Werkstoffe und ihre Verarbeitung" (Dental materials and their processing), Vol. 2, p. 135 et seq, Hüthig Verlag, 5th Edition 1985), is applied.

In a similar fashion, the preparations according to the invention can be used for attaching crowns, bridges and similar aids.

EXAMPLE 1

Synthesis of the new formylpiperazine group-containing (meth)acrylic acid esters as exemplified by N-formyl-N'-5, (methacryloyloxyethyl)piperazine Preliminary step 80 g (1.33 mol) of methyl formate were added dropwise to a stirred solution of 520.8 g (4.00 mol) of N-2-hydroxyethylpiperazine in 500 ml of methanol and the mixture was heated to reflux for four hours. After stripping easily volatile constituents, the residue obtained was rectified at 0.1 mm Hg, 169.6 g (81% of theory) of N-formyl-N'-2-hydroxyethylpiperazine being obtained between 135° and 140° C. in the form of a colorless liquid.

IR (film): $\nu = 3400, 2930, 1680, 1660, 1440, 1400, 1275, 1218, 1142, 1047, 1008, 760$ cm$^{-1}$.

$^1$H-NMR (CDCl$_3$, 200 MHz): $\delta = 2.53$ $$(m, 6H, H_2CN\begin{matrix}\diagup CH_2 \\ \diagdown CH_2\end{matrix}),$$

3.26 (s, 1H, OH), 3.41, 3.56, (2t, J =5 Hz, each 2H, CON-CH$_2$), 3.67 (t, J =6 Hz, 2H, OCH$_2$), 8.03 (bs, 1H, CHO)ppm.

Subsequent step 105.5 g (1.01 mol) of methacryloyl chloride were added dropwise between −30° and −35° C. to a stirred solution of 160 g (1.01 mol) of N-formyl-N-'-2-hydroxyethylpiperazine, 111 g (1.10 mol) of triethylamine and 100 mg of 2,6-di-tert.-butyl-4-methylphenol in 300 ml of dichloromethane and the mixture was stirred for two hours at the same temperature. The precipitate which deposited was filtered off and the filtrate was washed with sodium chloride solution, dried and concentrated to give 166.8 g (73% of theory) of a clear oil of N-formyl-N'-(methacryloyloxyethyl)piperazine. It was possible to elute this with methanol in high purity from a silica gel column after separating small amounts of by-products with ether/n-hexane (6:4).

IR (film): ν=2940, 2800, 1725, 1675, 1442, 1400, 1318, 1294, 1194, 1160, 1010, 940 cm$^{-1}$.

$^1$H-NMR (CDCl$_3$, 200 MHz): δ=1.96 (bs, 3H, CH$_3$), 2.53

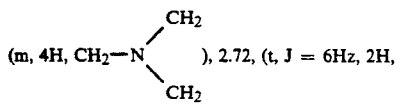

(m, 4H, CH$_2$—N(CH$_2$/CH$_2$)), 2.72, (t, J = 6Hz, 2H,

O—CH$_2$CH$_2$N), 3.39, 3.57, (2m, each 2H, H$_2$C—N—CO), 4.29 (t, J=6 Hz,2H,OCH$_2$), 5.59, 6.10 (2bs, each 1H, vinyl.-H), 8.02 (bs, 1H, CHO)ppm.

EXAMPLE 2

Synthesis of the new formylpiperazine group-containing (meth)acrylamides as exemplified by N-formyl-N'-(methacryloylaminoethyl)piperazine Preliminary step Corresponding to Example 1, 774.3 g (6.00 mol) of N-2-aminoethylpiperazine in 300 ml of methanol were reacted with 120.0 g (2.00 mol) of methyl formate and 151.6 g (48% of theory) of N-2-aminoethyl-N'-formylpiperazine were obtained at 0.1 mm Hg between 115 and 120° C. in the form of a yellowish liquid IR (Film): ν=3300, 2930, 2800, 1668, 1441, 1396, 1272, 1203, 1130, 1013 cm$^{-1}$.

$^1$H-NMR (CDCl$_3$, 2000 MHz): δ=1.64 (bs, 2H, NH$_2$), 2.47

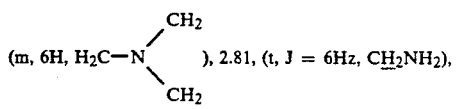

(m, 6H, H$_2$C—N(CH$_2$/CH$_2$)), 2.81, (t, J = 6Hz, CH$_2$NH$_2$), 3.40, 3.48 (2t, J =5 Hz, each 2H, CON—CH$_2$), 8.02 (s, 1H, CHO)ppm.

Subsequent step 117.9 g (0.75 mol) of N-2-aminoethyl-N'-formylpiperazine, 85.8 g (0.85 mol) of triethylamine and 100 mg of 2,6-di-tert.-butyl-4-methylphenol were reacted in 230 ml of dichloromethane with 78.4 g (0.75 mol) of methacryloyl chloride as described in Example 1 and the mixture was worked up. 73.9 g (44% of theory) of N-formyl-N'-(methacryloylaminoethyl)piperazine were obtained in this manner as a colorless oil.

IR (film): ν=3350, 2950, 2820, 1675, 1665, 1618, 1532, 1442, 1221, 1152, 101, 925 cm$^{-1}$.

$^1$H-NMR (CDCl$_3$, 200 MHz): δ=1.98 (bs, 3H, CH$_3$), 2.5

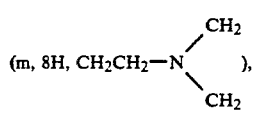

(m, 8H, CH$_2$CH$_2$—N(CH$_2$/CH$_2$)), 3.42, 3.56, (2t, each 2H, H$_2$C—N—CO), 5.35, 5.70 (2 bs, each 1H, vinyl.-H), 6.52 (bs, 1H, NH), 8.03 (s, 1H, CHO)ppm.

EXAMPLES 3 TO 6

Production of the preparations (II)

The adhesives according to the invention are produced by intensive mixing of the constituents shown in the following examples:

EXAMPLE 3

| 47 g | water |
|---|---|
| 53 g | N-formyl-N'-(methacryloyloxyethyl)piperazine |
| 159 mg | camphorquinone |

EXAMPLE 4

| 36 g | water |
|---|---|
| 48 g | N-formyl-N'-(methacryloyloxyethyl)piperazine |
| 16 g | 25% strength by weight aqueous glutaraldehyde solution |
| 144 mg | camphorquinone |

EXAMPLE 5

| 48 g | water |
|---|---|
| 52 g | N-formyl-N'-(methacryloylaminoethyl)piperazine |
| 144 mg | camphorquinone |

EXAMPLE 6

| 37 g | water |
|---|---|
| 48 g | N-formyl-N'-(methacryloylaminoethyl)piperazine |
| 15 g | 25% strength by weight aqueous glutaraldehyde solution |
| 144 mg | camphorquinone |

EXAMPLE 7

Use

The suitability of the adhesives (II) corresponding to Examples 3 to 6 is tested by determining the bonding strength of the light-activated plastic filling material based on multi-functional methacrylic acid esters and barium aluminosilicate Lumifor ® on dentine which has been pretreated successively with the conditioning liquid (consisting of 81.2 g water, 1.7 g sodium hydroxide and 17 g disodium ethylenediaminetetraacetate dihydrate: 60 seconds action, rinsing with water, air drying), the adhesive (60 seconds action, air drying) and a sealant based on polyfunctional methacrylic acid esters (Bayer Resin L ®) (applying and distributing thinly in a stream of air).

Extracted human teeth kept in the moist state are used for the test. The teeth are embedded by casting in epoxy resin; a smooth dentine surface is produced by subsequent grinding. The subsequent grinding is carried out using carbon paper 1000.

In order to prepare a test specimen for measuring the bonding strength, a cylindrical split Teflon mold is clamped onto the dentine surface treated as described above (Scand. J. Dent. Res. 88, 348≃351 (1980)). A commercial plastic filling material is poured in as filling material. A no. 016 round drill clamped into a hole in a drill hole is attached to the Teflon mold and pressed from above into the material layer which is still in the process of hardening.

The entire arrangement is allowed to stand undisturbed at room temperature (25° C.) for 10 minutes, after which the drill holder and the Teflon mold are removed and the sample deposited under water at a temperature of 23° C. After 15 minutes, the sample containing the drill is mounted in an Instron tensile test apparatus (Scand. J. Dent. Res. 88, 348-351 (1980)); a tensile strength measurement is carried out at a velocity of 1 mm/min. The tensile strength is calculated by dividing the load applied on fracture of the filling by the cross-sectional area in the fracture surface of the test specimen. 5 measurements on test specimens were carried out in each case.

The results are summarized in the following table:

| Preparation according to Example No. | Tensile bonding strength [N/mm$^2$] |
|---|---|
| 3 | 7 ± 2 |
| 4 | 12 ± 3 |
| 5 | 9 ± 2 |
| 6 | 9 ± 3 |

It is understood that the specification and examples are illustrative but not limitative of the present invention and that other embodiments within the spirit and scope of the invention will suggest themselves to those skilled in the art.

We claim:

1. An adhesive composition for the treatment of a collagen-containing material comprising a formylpiperazine group-containing (meth)acrylic acid derivative of the formula

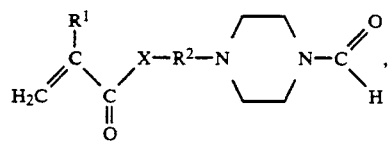

in which $R^1$ is hydrogen or methyl,
$R^2$ is a divalent aliphatic or cycloaliphatic radical, and
X is —O— or —NH—.
and an initiator, coactivator, carbonyl compound, filler, stabilizer, inhibitor, light screen, colorant, pigment or fluorescent substance.

2. A composition according to claim 1, in which $R^2$ is ethylene.

3. A composition according to claim 2, in which $R^2$ is cyclohexylene.

4. A composition according to claim 1, wherein such derivative is N-formyl-N'-(methacryloyloxyethyl)piperazine of the formula

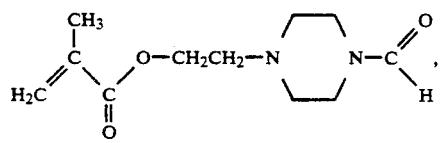

5. A composition according to claim 1, wherein such derivative is N-formyl-N'-(methacryloylaminoethyl)-piperazine of the formula

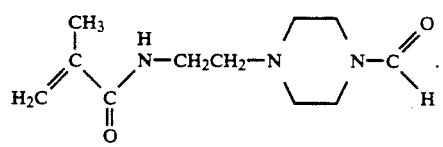

6. An adhesive composition for the treatment of a collagen-containing material comprising a formylpiperazine group-containing (meth)acrylic acid derivative according to claim 1 and a cross-linkable (meth)acrylic acid ester.

7. In the adhesion of a first material to a collagen-containing second material employing an adhesive, the improvement wherein said adhesive comprises a composition according to claim 1.

8. The method according to claim 8, wherein the collagen-containing second material is a bone or tooth.

9. The method according to claim 8, wherein the derivative is
N-formyl-N'-(methacryloyloxyethyl) piperazine or
N-formyl-N'-(methacryloylaminoethyl) piperazine.

* * * * *

UNITED STATES PATENT AND TRADEMARK OFFICE
CERTIFICATE OF CORRECTION

PATENT NO. : 5,068,264

DATED : November 26, 1991

INVENTOR(S) : Muller et al.

It is certified that error appears in the above-identified patent and that said Letters Patent is hereby corrected as shown below:

Col. 26, line 10   Delete " claim 2 " and substitute -- claim 1 "

Col. 26, line 43   Delete " claim 8 " and substitute -- claim 7 --

Col. 26, line 45   Delete " claim 8 " and substitute -- claim 7 --

Signed and Sealed this

Twenty-first Day of September, 1993

Attest:

BRUCE LEHMAN

Attesting Officer

Commissioner of Patents and Trademarks